(12) United States Patent
Stubblefield et al.

(10) Patent No.: US 10,900,007 B2
(45) Date of Patent: Jan. 26, 2021

(54) BIOREACTOR SYSTEM

(71) Applicant: GEORGIA STATE UNIVERSITY RESEARCH FOUNDATION, INC., Atlanta, GA (US)

(72) Inventors: Bryan Stubblefield, Atlanta, GA (US); Eric Gilbert, Decatur, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 414 days.

(21) Appl. No.: 15/780,487

(22) PCT Filed: Dec. 1, 2016

(86) PCT No.: PCT/US2016/064409
§ 371 (c)(1),
(2) Date: May 31, 2018

(87) PCT Pub. No.: WO2017/096035
PCT Pub. Date: Jun. 8, 2017

(65) Prior Publication Data
US 2018/0346863 A1   Dec. 6, 2018

Related U.S. Application Data

(60) Provisional application No. 62/261,591, filed on Dec. 1, 2015.

(51) Int. Cl.
*C12M 1/06* (2006.01)
*B01F 13/08* (2006.01)
*C02F 3/00* (2006.01)

(52) U.S. Cl.
CPC ........... *C12M 27/02* (2013.01); *B01F 13/089* (2013.01); *B01F 13/0827* (2013.01); *C02F 3/006* (2013.01); *C02F 2209/02* (2013.01)

(58) Field of Classification Search
CPC .............................. C12M 27/02; B01F 13/0827
See application file for complete search history.

(56) References Cited

U.S. PATENT DOCUMENTS

| | | | |
|---|---|---|---|
| 2,549,121 A | 4/1951 | Osterheld et al. | |
| 3,572,651 A | 3/1971 | Harker et al. | |
| (Continued) | | | |

FOREIGN PATENT DOCUMENTS

| | | |
|---|---|---|
| CN | 202212138 U | 5/2012 |
| CN | 203700346 U | 7/2014 |
| (Continued) | | |

OTHER PUBLICATIONS

International Preliminary Report on Patentability conducted in International Application No. PCT/US2016/064409, dated Jun. 14, 2018.

(Continued)

*Primary Examiner* — Jonathan M Hurst
(74) *Attorney, Agent, or Firm* — Meunier Carlin & Curfman LLC

(57) ABSTRACT

According to various implementations, the bioreactor system includes a bioreactor vessel, an impeller for stirring contents within the vessel, a temperature control source for controlling the temperature of the contents of the vessel, an aeration system for supplying air to the vessel, and one or more data loggers. According to certain implementations, the impeller is a novel impeller design that spins more smoothly and rapidly than known impellers. In addition, the bioreactor system is modular, durable, and relatively inexpensive compared to existing bioreactor systems, which allows for bench-scale implementation, use with differently sized bioreactor vessels, and accessibility to more educational programs, according to some implementations.

19 Claims, 5 Drawing Sheets

(56) References Cited

U.S. PATENT DOCUMENTS

| | | | |
|---|---|---|---|
| 3,649,465 A | 3/1972 | Scharf et al. | |
| 4,355,906 A | 10/1982 | Ono et al. | |
| 4,382,685 A | 5/1983 | Pearson | |
| 2002/0009803 A1 | 1/2002 | Vajta | |
| 2007/0286015 A1 | 12/2007 | Markle et al. | |

FOREIGN PATENT DOCUMENTS

| | | |
|---|---|---|
| EP | 0053869 | 6/1982 |
| EP | 0222644 A1 | 5/1987 |
| GB | 2196800 A | 5/1988 |

OTHER PUBLICATIONS

International Search Report and Written Opinion issued in related International Application No. PCT/US2016/064409 dated Apr. 6, 2017.

BIOREACTOR SYSTEM

CROSS REFERENCE TO RELATED APPLICATION

This application is a national stage application filed under 35 U.S.C. § 371 of International Application No. PCT/US2016/064409 filed Dec. 1, 2016, which claims priority to U.S. Patent Application No. 62/261,591, entitled "Bioreactor System," and filed on Dec. 1, 2015, the content of which are herein incorporated by reference in their entirety.

BACKGROUND

Bioreactors hold a central place in the production of pharmaceuticals, food, and biofuels and in the treatment of waste water. In spite of their significance to industry, bioreactors are rarely part of undergraduate learning curricula due to their high cost and/or complex and fragile equipment.

Bioreactors typically include an impeller for stirring a liquid medium disposed within a bioreactor vessel. For example, in U.S. Pat. No. 3,649,465 to Scharf, et al., a plastic bearing is carried on a spindle at its upper end, and the outer circumferential surface of the plastic bearing is in bearing engagement with an inner surface of a non-rotating shroud. The spindle rotates in response to a rotating magnetic force acting on an agitator hub coupled to a distal end of the spindle. Similarly, in U.S. Pat. No. 3,572,651 to Harker, an impeller shaft is supported by a bearing block at a top of the shaft. A holder element that includes a magnetized impeller is coupled to the bottom of the impeller shaft, and the impeller shaft rotates in response to a rotating magnetic force acting on the magnetized impeller. However, these arrangements are subject to wobbling during rotation, which can stop rotation of the impeller and compromise the contents of the bioreactor vessel.

Therefore, there is a need in the art for a more durable and modular bioreactor.

BRIEF SUMMARY

Various implementations include an impeller for a bioreactor vessel. The impeller includes a cylindrical hollow tube, a magnetic stir bar, an axle, and first and second radial spacers. The cylindrical hollow tube has a proximal end and a distal end along a longitudinal axis extending through the cylindrical tube and defines an inner diameter. The magnetic stir bar is disposed adjacent the distal end of the tube. The axle extends through a portion of the length of the cylindrical tube. The axle has a longitudinal axis that is collinear with the longitudinal axis of the cylindrical tube and a distal end and proximal end, and the distal end of the axle is axially spaced apart from the magnetic stir bar. The first radial spacer is disposed adjacent the distal end of the axle, and the second radial spacer is disposed adjacent the proximal end of the cylindrical tube. Each radial spacer has an outer radial surface and an inner radial surface that is disposed adjacent the axle. At least a portion of the outer radial surface engages the inner diameter of the cylindrical hollow tube. The axle is stationary and the cylindrical tube rotates about its longitudinal axis and the longitudinal axis of the axle in response to a rotational magnetic force received by the magnetic stir bar.

In some implementations, the impeller further includes a cap that includes an end wall and a cylindrical side wall that extends axially from an edge of the end wall. The cap further defines an opening in a center of the end wall, wherein the side wall engages the proximal end of the cylindrical tube and the proximal end of the axle extends through the opening in the center of the end wall of the cap, and the cap rotates with the cylindrical tube about the axle. The side wall of the cap defines a plurality of screw threads, and the proximal end of the cylindrical tube defines a plurality of mating screw threads for engaging the screw threads of the side wall of the cap. In some implementations, the impeller includes a dampening ring disposed around a portion of the axle. The dampening ring has a diameter that is greater than a diameter of the opening in the end wall of the cap and is disposed axially adjacent an axial inner surface of the end wall. The axial inner surface of the end wall faces towards the distal end of the hollow cylindrical tube. In some implementations, the dampening ring comprises an elastomeric material. And, in some implementations, an axial position of the dampening ring along the axle is adjustable.

In some implementations, the at least a portion of the outer radial surface of each radial spacer frictionally engages the inner diameter of the cylindrical tube. In some implementations, the axle defines a smooth outer radial surface portion and a threaded outer radial surface portion, and the smooth outer radial surface portion is disposed within the cylindrical tube and at least a portion of the threaded outer radial surface portion is disposed adjacent and axially past the proximal end of the cylindrical tube.

In some implementations, the impeller includes one or more additional radial spacers disposed axially between the first and second radial spacers. The one or more additional radial spacers each have an outer radial surface, and at least a portion of the outer radial surface engages the inner diameter of the cylindrical tube. The one or more additional radial spacers are axially spaced apart from each other and the first and second radial spacers so as to evenly distribute the mass of the radial spacers along the axle. And, the spacing between the one or more additional radial spacers is selected to maintain smooth and stable rotation about the axle, according to some implementations. For example, in certain implementations, the impeller includes a third radial spacer.

In some implementations, the first radial spacer is disposed within an upper half of the cylindrical hollow tube, and the second radial spacer is disposed within a lower half of the cylindrical hollow tube. The upper half of the tube is axially above a plane that bisects the longitudinal axis of the cylindrical hollow tube between the proximal and distal ends of the cylindrical hollow tube, and the lower half of the tube is axially below the plane.

In some implementations, the radial spacers comprise ball bearings and/or nuts.

In some implementations, the impeller also includes axial stop members. For example, a first axial stop member is disposed axially adjacent and distally of the first radial spacer, and the second axial stop member is disposed axially adjacent and distally of the second radial spacer. The axial stop members prevent axial movement of the radial spacers toward the distal end of the axle.

In some implementations, the magnetic stir bar is disposed 1 millimeter below the distal end of the axle.

In some implementations, a distal surface of the second radial spacer is disposed 1 mm to 5 mm from the distal end of the tube.

Other various implementations include a bioreactor system that includes a bioreactor vessel, a vessel cap, and an impeller, such as the impeller described above. The bioreactor vessel has a bottom surface and one or more side walls extending from the bottom surface. The one or more side walls define at least one central opening axially opposite the bottom surface. The vessel cap is configured for engaging the one or more side walls to close off the central opening of the vessel, and the vessel cap includes top surface and one or more side walls that extend from the top surface and engage with the one or more side walls of the vessel. The proximal end of the axle of the impeller extends through an opening defined in the top surface of the vessel cap and is secured relative to the top surface of the vessel cap, and the distal end of the cylindrical hollow tube is spaced apart from and axially above the bottom surface of the bioreactor vessel.

In some implementations, the distal end of the cylindrical hollow tube is axially spaced apart from the bottom surface of the bioreactor vessel by at least three centimeters. In some implementations, a longitudinal axis of the magnetic stir bar is disposed axially above the bottom surface of the bioreactor vessel by at least three centimeters.

In some implementations, the bioreactor system includes a magnetic stir plate on which the vessel is disposable.

In some implementations, the bioreactor system further includes a temperature control system. The temperature control system includes an open ended container in which a liquid is disposed, a pump, a temperature control source, and one or more conduits extending between the open ended container, the pump, and the temperature control source. The bottom surface and at least a portion of the side walls of the vessel are disposable within the open ended container such that the liquid surrounds the portion of the side walls of the vessel, and the pump causes the liquid to flow between the open ended container and the temperature control source.

In some implementations, the temperature control source includes a second container and a heater plate. The second container is disposed on the heater plate, and heat is transferred between the fluid in the second container and the heater plate. The temperature of the heater plate is adjustable, according to some implementations. In addition, the heater plate is selectably used as a heat sink or a heat source, according to some implementations.

In some implementations, a second magnetic stir bar is disposed within the second container of the temperature control source, and the heater plate includes at least one rotatable magnet for causing the second magnetic stir bar to spin within the second container.

In some implementations, the liquid is water or glycerin.

In some implementations, the open ended container and the liquid are transparent.

In some implementations, a speed of the pump is adjustable.

In some implementations, the temperature control system is selectable to heat or cool contents of the vessel. For example, in some implementations, the temperature control source comprises a second container and a heating plate, and the heating plate transfers heat to the liquid in the second container.

In some implementations, the bioreactor system includes an aeration system. The aeration system includes an air pump, a safety container, and conduits extending between the air pump and the safety container and from the safety container to the vessel. The safety container defines a first port in fluid communication with the conduit extending between the pump and the safety container, a second port in fluid communication with the conduit extending between the safety container and the vessel, and a third port in fluid communication with a safety valve that opens in response to the air pressure inside of the safety container reaching a predetermined threshold and allows air to pass to the atmosphere.

In some implementations, the cap defines one or more ports through which one or more probes or conduits are insertable into the bioreactor vessel.

In some implementations, the one or more ports comprises a sample collection port.

BRIEF DESCRIPTION OF THE DRAWINGS

Various implementations are explained in detail in the following exemplary drawings. The drawings are merely exemplary to illustrate the structure of exemplary systems and methods and certain features that may be used singularly or in combination with other features. The invention should not be limited to the implementations shown.

DETAILED DESCRIPTION

According to various implementations, the bioreactor system includes a bioreactor vessel, an impeller for stirring contents within the vessel, a temperature control source for controlling the temperature of the contents of the vessel, an aeration system for supplying air to the vessel, and one or more data loggers. According to certain implementations, the impeller is a novel impeller design that spins more smoothly and rapidly than known impellers. In addition, the bioreactor system is modular, durable, and relatively inexpensive compared to existing bioreactor systems, which allows for bench-scale implementation, use with differently sized bioreactor vessels, and accessibility to more educational programs, according to some implementations.

Figure 1:
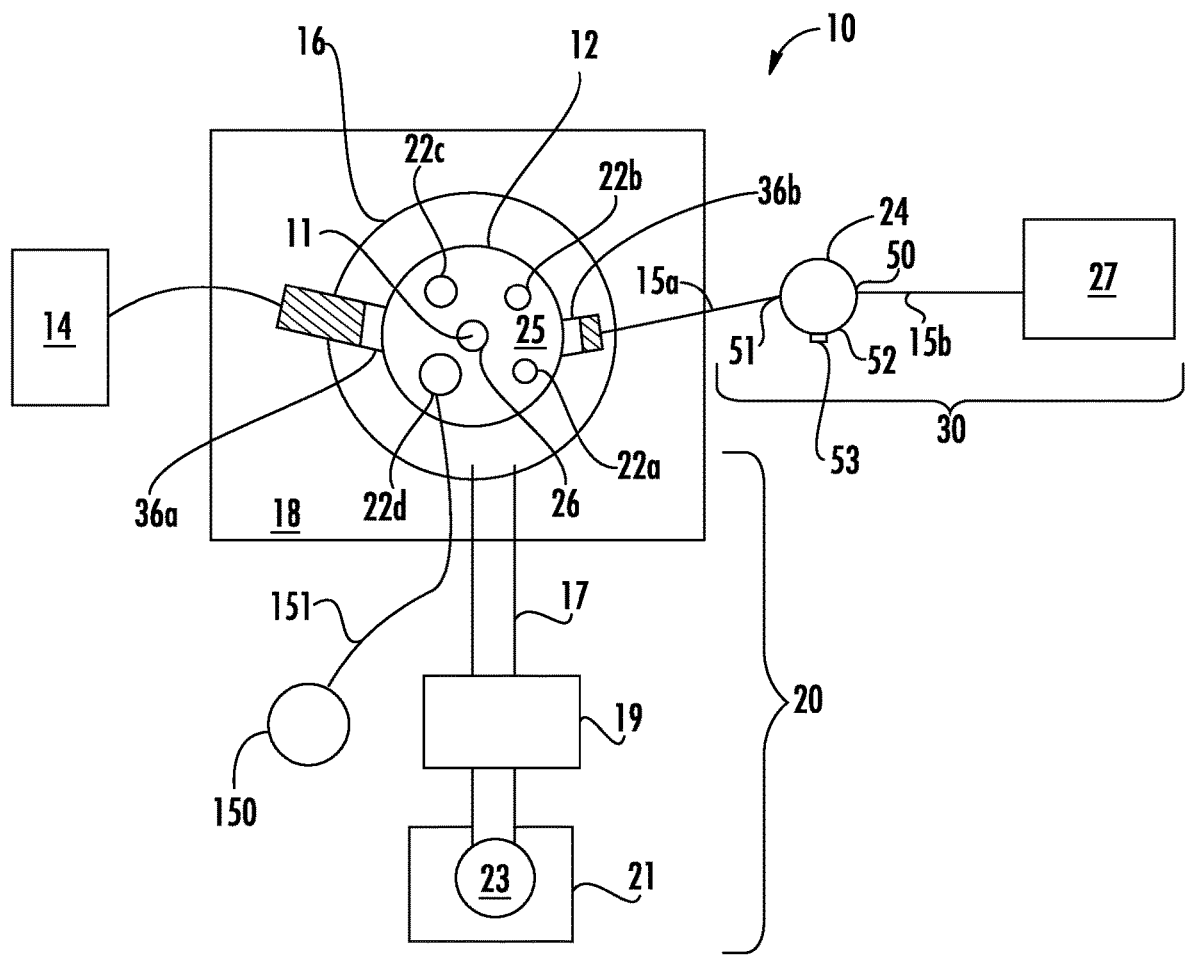
FIG. 1 illustrates a schematic diagram of a bioreactor system according to one implementation.

For example, FIG. 1 illustrates a top view schematic diagram of a bioreactor system 10 according to one implementation. The bioreactor system 10 includes a bioreactor vessel 12, a data logger 14, a magnetic stir plate 18, a temperature control system 20, and an aeration system 30.

Figure 2:
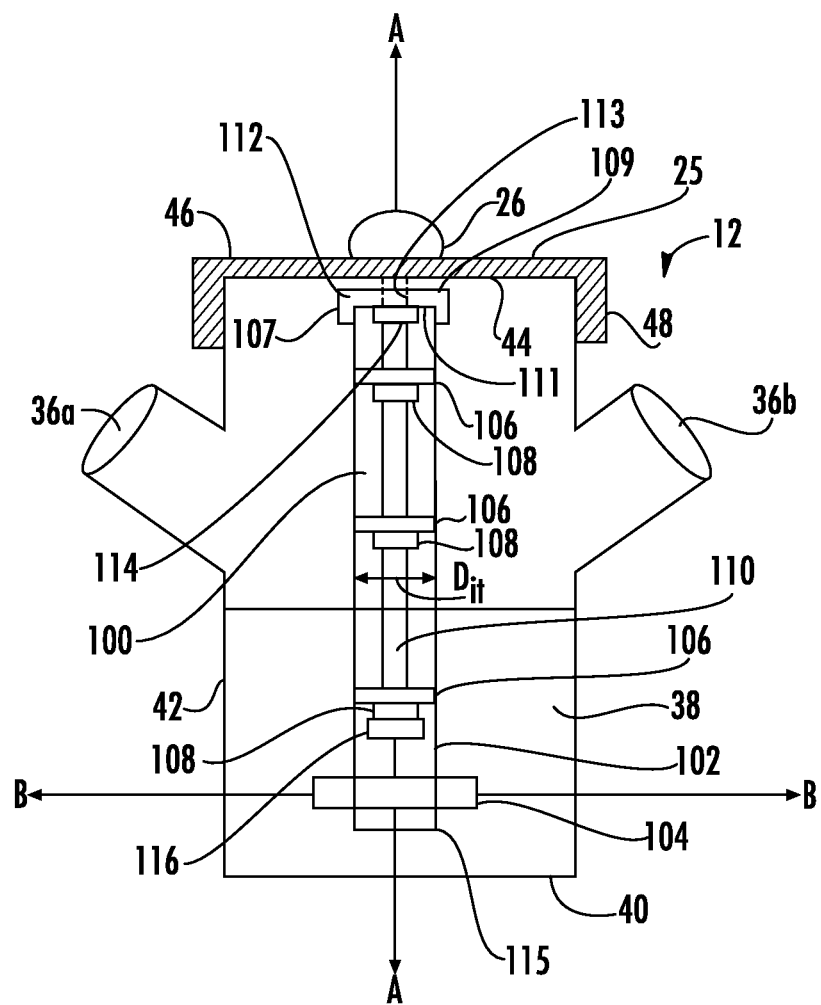
FIG. 2 illustrates a schematic diagram of an impeller according to one implementation.

The bioreactor vessel 12 shown in FIGS. 1 and 2 includes a bottom surface 40 and a side wall 42 that extends from the bottom surface 40. The side wall 42 is substantially cylindrical, but in other implementations, the vessel may include one or more side walls and have other suitable shapes. The side wall 42 defines at least one central opening 44 that is axially opposite the bottom surface 40. In addition, in some implementations, the side wall 42 may also define one or more additional openings, or ports, extending radially outwardly from the side wall 42, such as port 36a and port 36b. These ports may be used to access the interior of the bioreactor vessel 12. For example, as shown in FIG. 1, a temperature probe is disposed within the vessel 12 via port 36a and is in communication with data logger 14, which is disposed outside of the vessel 12. And, the aeration system 30 is in communication with the interior of the vessel 12 via port 36b. Because the system 10 is modular, other types of data may be collected via the ports 36a, 36b and other types of sub-systems may be in communication with the interior of the vessel 12 via the ports 36a, 36b, such as, for example, an exhaust gas collection system. In some implementations, the vessel 12 is made of glass or other suitable transparent, non-reactive material.

A vessel cap 25 is disposed adjacent the central opening 44. The vessel cap 25 includes a top wall 46 and a side wall 48 that extends axially from the top wall 46. The side wall 48 of the vessel cap 25 engages the side wall 42 of the vessel 12. For example, a radially inward surface of the side wall 48 defines threads that mate with threads defined on a radially outward surface of the side wall 42 to couple the vessel cap 25 to the vessel 12 adjacent the opening 44. In other implementations, alternative mechanisms for coupling the cap 25 adjacent to the central opening 44 of the vessel 12 may be used, such as a friction fit, snap fit, clamp, etc. The vessel cap 25, according to various implementations, is made of ceramics, plastics, metal (e.g., steel), other suitable rigid material, or a combination thereof.

In addition, the top wall 46 of the vessel cap 25 may be provided with one or more ports, such as ports 22a, 22b, 22c, 22d shown in FIG. 1, for accessing an interior of the vessel 12 without removing the cap 25. According to some implementations, the ability to remove the cap 25 from the vessel 12 allows the vessel 12 to be cleaned and reused for various experiments, and caps having various port arrangements are selected (or created) based on the needs of the experiment.

For example, the ports 22a-22d may include a sample collection port through which samples of the contents of the vessel 12 may be extracted without removing the cap 25 or stopping operation of the impeller 100, a material insertion port through which material may be inserted into the vessel 12, and/or a probe port through which a probe for collecting data related to the contents of the vessel 12 may be inserted. In addition, one of the ports 22a-22d may be in communication with an exhaust collection container 150 via a conduit 151. Exhaust gases created within the vessel 12 may flow out of the vessel 12 through port 22d, for example, and conduit 151 to the exhaust collection container 150, and the gas may be extracted from the container 150 for analysis. In some implementations, the ports 22a-22d include fittings, such as metal caps (e.g., brass, steel), and/or conduits.

One or more of the ports 22a-22d are usable to aseptically withdraw fluids from the bioreactor vessel, according to certain implementations. For example, in implementations in which one of ports 22a-22d is a sample collection port, the sample collection port includes a fitting (e.g., a brass fitting) within the port opening defined in the cap 25 and a glass tube having a first end and a second end. The first end of the glass tube is disposed within the vessel 12 and adjacent the bottom surface 40 of the vessel 12 (e.g., in contact with or spaced above the bottom surface 40), and the second end of the glass tube is disposed outside of the vessel 12 and cap 25. The portion of the glass tube that extends outside of the cap 25 may be bent (e.g., pre-bent or bent using a glass flame) to improve access to the sample port, for example. If necessary, a section of elastomeric tubing (e.g., BPT) or other suitable sealing material is disposed between the glass tube and the fitting to seal the radial space therebetween. The second end of the glass tube is coupled to an inlet opening of a three-way valve (e.g., a stopcock), according to one implementation. The valve further includes a distal tip opening that is axially opposite and spaced apart from the inlet opening and a central opening that is axially between and radially spaced apart from the inlet opening and the distal tip opening. A filter (e.g., a 0.22 micrometer filter) is coupled to the distal tip opening of the valve to keep the vessel 12 aseptic during sampling. And, a syringe (e.g., a luer-lock syringe) is insertable through the central opening to collect a sample. When samples are not being taken, the central opening may be sealed with a plug (e.g., a female luer-lock plug).

A length of elastomeric tubing (e.g., BPT) may be used to couple an air stone (sparger) to the second end of the glass tube when the sample port is used for air transport.

The air exhaust port, such as port 22d, includes a fitting (e.g., a brass fitting) within the port opening defined in the cap 25 and conduit 151 (e.g., a latex tube). A first end of the conduit 151 is disposed in the fitting. A hose clamp is used to secure the conduit in some implementations. The second end of the conduit 151 is disposed within an exhaust collection container 150 via a plug disposed within the opening of the container 150. The plug may include a porous material (e.g., foam or porous cork plug) if the exhaust gases are not be toxic, or the plug may include a non-porous material (e.g., an elastomeric material (e.g., rubber) or non-porous cork plug) if the gases are toxic.

In addition, an impeller, such as impeller 100 shown in FIG. 2, is coupled to the cap 25 through port 26 defined by the cap 25. The port 26 shown in FIG. 1 is defined at a center 11 of the cap 25. FIG. 2 shows a side view of a portion of the bioreactor system 10 and shows a partially sectional view of cap 25. Impeller 100 includes a cylindrical hollow tube 102, a magnetic stir bar 104, an axle 110, at least two radial spacers 106 disposed along the axle 110, a cap 112, and a dampening ring 114. The cylindrical hollow tube 102 has a proximal end 111 and a distal end 115 along a longitudinal axis A-A extending through the tube 102, and the tube 102 defines an inner diameter D. The distal end 115 of the tube 102 is open in the implementation shown in FIG. 2, but in other implementations, it may be closed. For example, an end cap (not shown) may be coupled to the distal end 115 of the tube 102. The end cap according to one implementation may be a rubber cap or other suitable material (e.g., an elastomeric material or cork). The cap 112 is coupled to the proximal end 111 of the tube 102 via a side wall 107 of the cap 112 that extends from an end wall 109 of the cap 112. For example, a radially inner surface of the side wall 107 of the cap 112 and a radially outer surface of the proximal end 111 of the tube 102 may define screw threads that engage each other for coupling the cap 112 to the tube 102. When the cap 112 is coupled to the tube 102, the cap 112 rotates with the cylindrical tube 102 about the axle 110. In other implementations, the cap 112 may be coupled to the proximal end 111 of the tube 102 via a friction fit, a clamp, a snap fit, or other suitable coupling mechanism.

In one implementation, the tube 102 is formed from a conical tube (e.g., a 15 mL conical tube), and the cap 112 is the cap that is provided with the conical tube. The closed, conical shaped end of the conical tube is removed, creating a cylindrical tube having two open ends. However, in other implementations, the tube 102 is formed as a cylindrical tube with one or two open ends, and the cap 112 is formed to engage one of the open ends of the tube.

The magnetic stir bar 104 is disposed adjacent the distal end 115 of the tube 102. For example, the stir bar 104 may extend through two openings defined in the tube 102, wherein an axis B-B extending through a center of each opening is perpendicular to the longitudinal axis A-A of the tube 102. The distance between the axis B-B and bottom surface 40 of the vessel 12 may be 3 centimeters to 5 centimeters (e.g., 4 cm). For example, in an implementation in which the centers of the openings defined in the tube 102 are defined 1 centimeter axially above the distal end 115 of the tube 102, the distal end 115 of the tube 112 may be disposed 3 centimeters above the bottom surface 40 of the vessel 12. In some implementations, the stir bar 104 is fit securely within the openings along the B-B axis. For example, if the inner diameter of the openings and the outer diameter of the stir bar allow for movement of the stir bar 104 within the openings, an elastomeric material (e.g., tape, BPT tubing) can be disposed between the stir bar 104 and the openings to prevent movement. However, in other implementations, the distance between the axis B-B and the bottom surface 40 of the vessel 12 may be less than 3 cm or greater than 5 cm depending on the strength of the magnetic force of the stir plate.

Axle 110 extends through a portion of the length of the tube 102 and has a longitudinal axis that is co-linear with axis A-A. The end wall 109 defines an opening 113 through a center thereof, and a proximal end of the axle 110 extends through the opening 113 defined in the cap 112. A distal end 116 of the axle 110 is axially spaced apart from the magnetic stir bar 104. For example, in one implementation, the distal end 116 of the axle 110 is spaced at least 1 millimeter axially above an upper radial surface of stir bar 104. This spacing between the distal end 116 of the axle 110 and the stir bar 104 prevents the stir bar 104 from contacting the distal end 116 of the axle 110 at initial startup of the magnetic stir plate 18, during which the bar 104 may be urged axially upwardly away from the magnetic stir plate 18. The proximal end of the axle 110 also extends through opening 26 defined in the vessel cap 25. In the implementation shown in FIG. 2, a radially outward surface of the proximal end of the axle 110 defines threads that are engaged with a threaded dome nut for coupling the axle 110 to the cap 25. In an alternative implementation, the opening 26 in the vessel cap 25 includes an elastomeric stopper that defines an opening, and the proximal end of the axle 110 extends through the opening in the elastomeric stopper and is prevented from axial movement relative to the stopper by a frictional force of the stopper onto the axle 110. Other implementations may include other suitable mechanisms for coupling the axle 110 to the cap 25.

In one implementation, the axle 110 is a bolt having a first end, a second end, a threaded outer radial surface adjacent the first end, and a smooth outer radial surface adjacent the second end. The bolt may also include a head at the second end that has a diameter that is greater than portion of the bolt between the first and second ends.

At least two radial spacers 106 are disposed along a length of the axle 110 and are axially spaced apart from each other. The cap 112 and at least a portion of the radial spacers 106 serve to maintain the perpendicular orientation of the rotation axis A-A of the tube 102 with the magnetic stir plate 18. For example, a first radial spacer 106 is disposed adjacent the distal end 115 of the axle 110 and a second radial spacer 106 is disposed adjacent the proximal end 111 of the cylindrical tube 102. The first radial spacer 106 adjacent the distal end 115 of the axle 110 limits the horizontal movement of the tube 102, which increases the smoothness and stability of the rotation of the tube 102 about the axle 110. In some implementations, one or more additional radial spacers are disposed axially between the first and second radial spacers 106. For example, in one implementation, a third radial spacer 106 is disposed axially between the first and second radial spacers 106. The number of radial spacers 106 are selected based on the length of the tube 102 and/or the length of the axle 110.

Figure 6A:
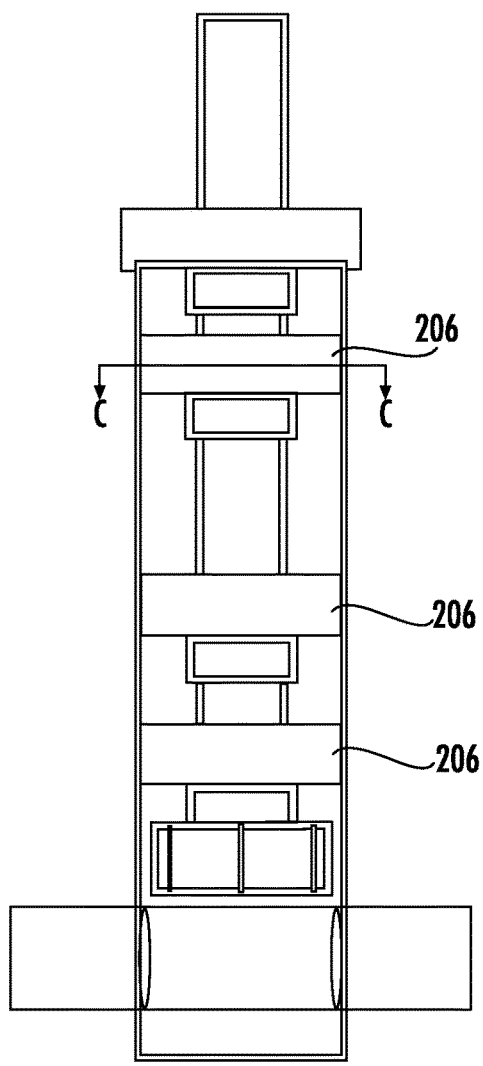
FIGS. 6A and 6B illustrate a side view and a cross sectional view through the C-C line of an impeller according to another implementation.
Figure 6B:
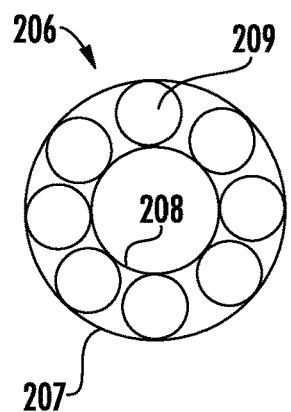

Each radial spacer 106 includes an outer radial surface that frictionally engages an inner diameter of the tube 102 and an inner radial surface that is disposed adjacent to and is rotatable about the axle 110. The spacers 106 may include, for example, roller bearings, hexagonal nuts, trilobal or clover shaped spacers, or any other suitable radial spacer mechanism that allows smooth and stable rotation of the tube 102 about the axle 110. For example, in the implementation shown in FIGS. 6A and 6B, impeller 200 includes ball bearings 206 as radial spacers. Each ball bearings 206 includes an outer race 207 and an inner race 208 and a plurality of balls 209 disposed between the outer race 207 and inner race 208.

In other implementations, the spacers 106 may be formed of any biocompatible material, such as, for example, metal, plastic, or composite materials. In addition, in other implementations, an outer radial surface of the axle 110 adjacent the spacers 106 may define a smooth surface to allow smooth rotation of the spacers 106 and tube 102 about the axle 110. For example, the outer radial surface of the axle 110 adjacent the spacers 106 may include a biocompatible lubricant or coating, such as silicone.

Furthermore, the spacers 106 are axially spaced apart from each other so as to evenly distribute the mass of the spacers 106 along the axle 110. This spacing provides smooth and stable rotation (e.g., prevents wobbling) of the impeller 100 within the vessel 12, which provides for a more consistent operation of the bioreactor vessel 12. As one example, one radial spacer 106 is disposed within an upper half of the tube 102, and another radial spacer 106 is disposed within a lower half of the tube 102, wherein the upper half is axially above a plane that bisects the longitudinal axis of the tube 102 between the proximal end 111 and distal end 115 of the tube 102, and the lower half is axially below the plane.

To prevent axial movement of the radial spacers 106 and tube 102, axial stops 108 are disposed around axle 110 axially below each radial spacer 106. The axial stops 108 have an outer diameter that is bigger than an inner diameter of the spacers 106. In addition, a dampening ring 114 is disposed around the axle 110 axially adjacent the proximal end 111 of the tube 102 such that an axially inward surface of the end wall 109 of the cap 112 rests on an axially upper surface of the ring 114 due to gravity acting on the tube 102 and cap 112 and the magnetic attraction between the stir plate 18 and the stir bar 104. The ring 114 has an outer diameter that is larger than the inner diameter of opening 113 in the cap 112 to prevent axial movement of the cap 112 below the ring 114. The ring 114 and axial stops 108 maintain the spacing of the distal end 115 of the tube 102 above the bottom wall 40 of the vessel 12.

The ring 114 may be formed of a dampening material, such as an elastomeric material (e.g., BPT tubing), that absorbs vibration and can be moved axially along the axle 110 to adjust the distance between the magnetic stir bar 104 and the bottom wall 40 of the vessel 12 and/or the distal end 116 of the axle 110. When the stir plate 18 is turned on, the magnet force from the magnetic stir plate 18 may cause the magnetic stir bar 104 (and the tube 102) to move axially upwardly, or away from the bottom surface 40 of the vessel 12, briefly. When the tube 102 falls back into its normal position due to gravity and the attraction between the stir plate 18 and stir bar 104, the ring 114 absorbs the downward force from the cap 112 and prevents the tube 102 from vibrating axially.

The ability to adjust the axial location of the ring 114 is useful for finding the optimal distance, or "sweet spot", between the magnetic stir bar 104 and the bottom surface of the vessel 12. The sweet spot is the point at which the stir bar 104 remains magnetically coupled to the magnetic stir plate 18 and rotates smoothly and consistently. Outside of the sweet spot, the stir bar 104 and magnetic stir plate 18 are magnetically decoupled, resulting in inconsistent and uneven rotation. This optimal distance change depends on the magnetic stir plate 18 being used and/or the thickness of the bottom wall of the vessel 12. Thus, by adjusting the ring 114, the same impeller and/or axle can be used with various magnetic stir plate 18 and vessel 12. Furthermore, the axial stops 108 may be formed of the same material or a different material than the ring 114, and the axial location of the axial stops 108 are adjustable to adjust the axial spacing of the radial spacers 106.

In some implementations, the length of the impeller 100, as measured from the cap 112 to the distal end of the tube 102, is selected based on the size of the vessel 12, volume of contents within the vessel 12 to be stirred, and whether one or more probes (e.g., analytical probes) are to be disposed within the vessel 12. For example, in some implementations, the length of the impeller is selected to be between 3 and 10 inches (e.g., 4 inches, 8 inches). The axial location of the radial spacers 106 and the number of radial spacers 106 are adjustable depending on the length of the impeller 100 selected, according to some implementations.

The vessel 12 is disposed on a magnetic stir plate 18, which includes a rotating magnet therein to cause the magnetic stir bar 104 of the impeller 100 to spin around axis A-A. The stir plate 18 may be any suitable stir plate. For example, in some implementations, the stir plate 18 includes sufficient surface area to support the bioreactor vessel 12 (and the second container 23 if used) and induces sufficient rotation of impeller 100 to mix the contents within the vessel 12. In some implementations, the rotational speed is adjustable.

Figure 5A:
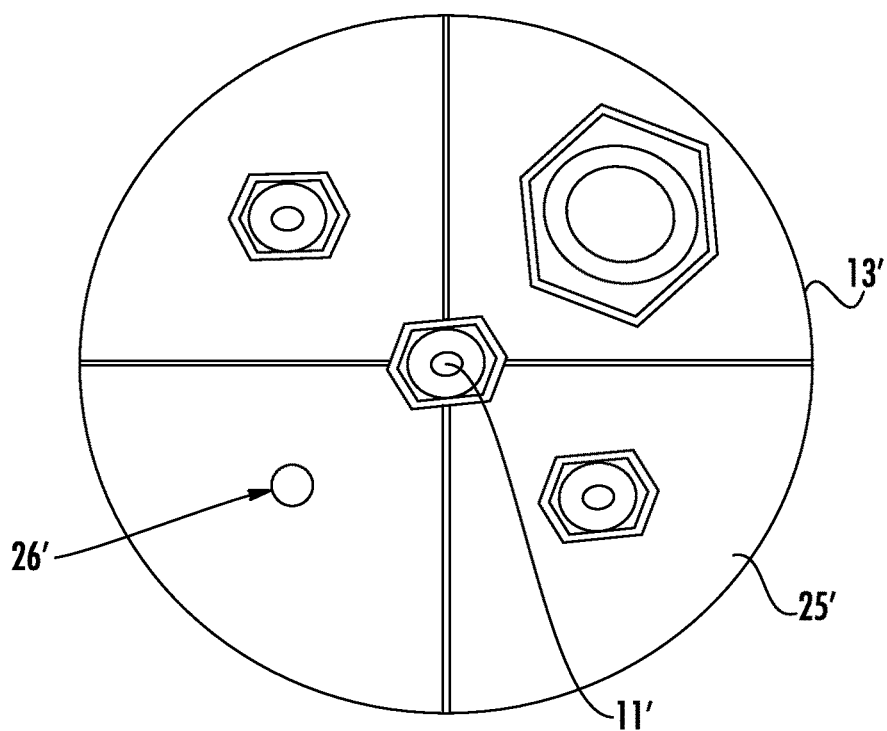
FIGS. 5A and 5B illustrate a top and side view, respectively, of a cap and impeller according to another implementation.
Figure 5B:
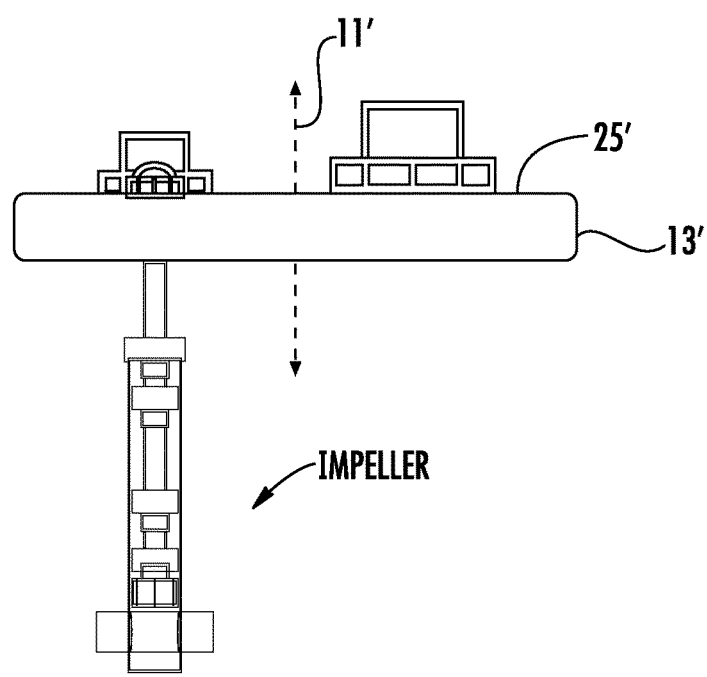

In the implementation described above in relation to FIG. 1, the port 26 is shown as being defined at a center 11 of the cap 25. However, in other implementations, the port 25 is defined at a location on the cap 25 that is offset from the center 11 of the cap 25 and is within a circle having a diameter equal to the cap diameter minus a length of the magnetic stir bar and centered on the center 11 of the cap 25. Placement of the port within this circle ensures that the magnetic stir bar does not contact the inner wall of the vessel. For example, FIGS. 5A and 5B illustrate a top view and a side view, respectively, of a cap 25' that defines port 26' between a center 11' of the cap 25' and an outer radial edge 13' of the cap 25'.

Figure 3:
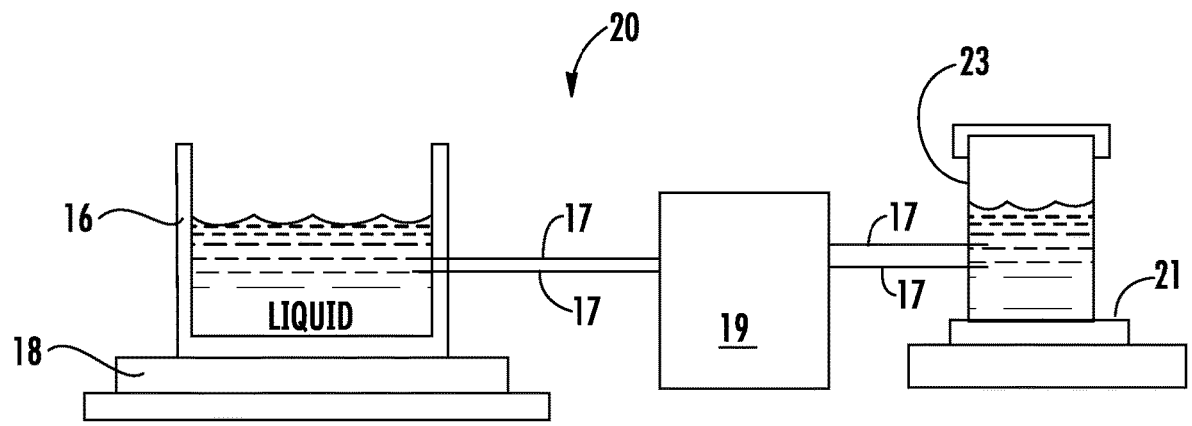
FIG. 3 illustrates a schematic diagram of a temperature control system according to one implementation.

The implementation shown in FIGS. 1 and 3 further includes temperature control system 20. The temperature control system 20 includes an open ended container 16 in which a liquid is disposed, a pump 19, a temperature control source, and conduits 17 extending between the open ended container 16, the pump 19, and the temperature control source. The temperature control source includes a heating plate 21 on which a second container 23 is disposed. However, in other implementations, the temperature control source includes a heating probe for inserting into the second container 23 or any other suitable mechanism for heating or cooling liquid flowing through the second container 23.

The bottom wall 40 and at least a portion of side wall 42 of the vessel 12 are disposed within the open ended container 16 such that the liquid surrounds an outer portion of the side wall 42. The pump 19 urges liquid to flow between the open ended container 16 and the second container 23. Heat is transferred between the liquid and the vessel 12 to regulate the temperature of the contents of the vessel 12. Furthermore, the temperature of the heat plate 21 is adjustable to adjust the temperature of the liquid flowing through the second container 23 and the open ended container 16. In some implementations, the heat plate 21 is usable as a heat sink to reduce the temperature of the contents of the vessel 12.

The open ended container 16 and the liquid therein are transparent, which allows for unobstructed observation of the vessel 12 and contents therein. Furthermore, the liquid in the open ended container 16 does not contact the contents of the vessel 12, and the type of liquid used in the temperature control system 20 is selected based on the temperature control needs for the system 10. For example, the liquid may be water or glycerin.

In some implementations, the heat plate 21 includes a rotating magnet such that the heat plate 21 functions as both a heat plate (and/or heat sink) and a magnetic stir plate. Further, an impeller, such as impeller 100 described above, is disposable within the second container 23 to stir the liquid.

In some implementations, the speed of the pump 19 is adjustable to increase or decrease the flow velocity through the temperature control system 20.

In some implementations, the second container 23 includes a rubber stopper that defines three ports therethrough. One conduit 17 extends through one of the ports for providing fluid to the open container 16, and another conduit 17 extends through one of the ports for returning fluid from the open container 16. These conduits 17 are in communication with pump 19, which may be, for example, a peristaltic pump. A third conduit 17 extends through the third port and serves as a gas exhaust.

In addition, in some implementations, the side wall of the open container 16 defines two openings that are circumferentially spaced apart from each other (e.g., diametrically opposed from each other), and conduits 17 extend through the openings for supplying fluid and for allowing fluid to flow to the pump 19 and the second container 23. In addition, to prevent heat loss, a cover may be disposed over the open end of the open container 16. For example, in some implementations, the cover is plastic, metal, or other suitable material and defines an opening for receiving the side wall 42 of the vessel 12.

Figure 4:
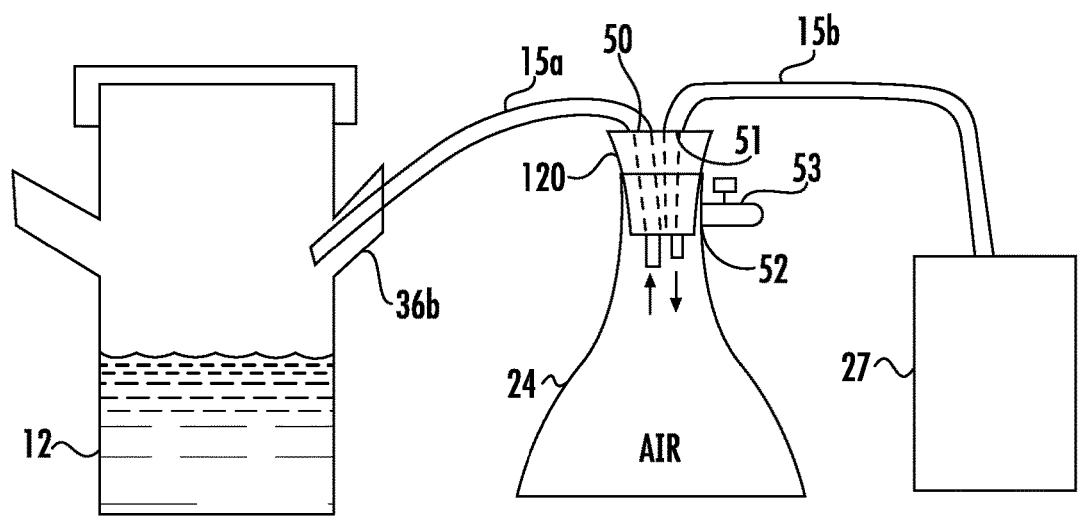
FIG. 4 illustrates a schematic diagram of an aeration system according to one implementation.

In some implementations, the bioreactor system 10 also includes an aeration system, such as aeration system 30 shown in FIGS. 1 and 4, to provide air flow within the vessel 12. The aeration system 30 includes an air pump 27, a safety container 24, and conduits 15a, 15b extending between the safety container 24 and the vessel 12 and between the safety container 24 and the air pump 27, respectively. The air pump 27 moves air through the system 30 by positive pressure. The safety container 24, which is in-line between the pump 27 and the vessel 12, includes a safety valve 53 that allows any buildup of air pressure to escape from the system 30 before reaching the vessel 12 to prevent an explosion. In various implementations, for example, the air pump 27 is a Top Fin 4000 aquarium pump or other suitable air pump. In addition, in various implementations, the safety valve 53 is any container that can withstand the build-up of pressure from the air pump 27 and provide a quick release. For example, in some implementations, a 2 or 3-way valve (e.g., a stopcock) could be used, wherein one opening is coupled to an air inlet conduit or port and a second opening is covered by a plug (e.g., an elastomeric (e.g., rubber) or cork plug) that dislodges when the pressure in the safety container 24 reaches a maximum allowable pressure.

According to one implementation, the safety container 24 includes a flask, such as a 25 mL flask, and a cork that seats within a neck of the flask. The cork 120, which may be formed of rubber or other elastomeric or suitable material, defines an outlet port 50 that is in fluid communication with the conduit 15a extending between the safety container 24 and the vessel 12 and an inlet port 51 that is in fluid communication with the conduit 15b extending between the pump 27 and the safety container 24. Air flows into the safety container 24 through the inlet port 51 and out of the safety container 24 through the outlet port 50.

The safety container 24 also defines a port 52 in fluid communication with safety valve 53 that opens in response to the air pressure within the safety container 24 reaching a predetermined threshold and allows air to pass to the atmosphere. In some implementations, the conduit 15a extending between the safety container and the vessel 12 extends into the vessel 12 through side port 36b, for example. In other implementations, all or a portion of the ports 50, 51, 52 may be defined in the cork 120 or in a side wall of the safety container 24. Furthermore, in other implementations, the safety container 24 includes any suitable container for receiving air from the air pump, allowing that air to pass through to the vessel 12, and having a safety valve in communication with the container 24 to allow air over a threshold pressure to escape to the atmosphere. In addition, according to some implementations, the conduits 15a, 15b include BPT tubing or tubing formed from another suitable material.

In some implementations, the aeration system 30 also includes a 0.22 micrometer filter disposed between the safety container 24 and the vessel 12. This filter is disposed, for example, adjacent the inlet of conduit 15a within the safety container 24 or adjacent the outlet of conduit 15a within vessel 12.

Data logger 14 stores data collected from the vessel 12. For example, data logger 14 may store data such as pH levels, oxidation-reduction potential, and/or temperature of the liquid medium in the vessel 12. In some implementations, an appropriate data measurement system is in electrical communication with the data logger 14 and provides the data to the data logger 14. The data logger 14 is also configured for communicating at least a portion of the stored data to a computing device, according to some implementations. The data logger 14 provides more flexibility in the type of data collected from the contents of the vessel 12 and how the collected data is stored and used. In some configurations, the data logger 14 could also be a computer.

Various components of the bioreactor system 10 described above may be packaged together in a kit for distribution, according to certain implementations. The kit may be assembled on site (e.g., in a laboratory or classroom).

While the foregoing description and drawings represent the certain implementations of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed implementations are, therefore, to be considered in all respects as illustrative and not restrictive, the scope of the invention being indicated by the appended claims and not limited to the foregoing description.

It will be appreciated by those skilled in the art that changes could be made to the implementations described above without departing from the broad inventive concept thereof. It is understood, therefore, that this invention is not limited to the particular implementations disclosed, but it is intended to cover modifications within the spirit and scope of the present invention, as defined by the following claims.

The invention claimed is:

1. An impeller for a bioreactor vessel comprising:
   a cylindrical hollow tube having a proximal end and a distal end along a longitudinal axis extending through the cylindrical tube, the cylindrical tube defining an inner diameter;
   a magnetic stir bar disposed adjacent the distal end of the tube;
   an axle extending through a portion of the length of the cylindrical tube, the axle having a longitudinal axis that is collinear with the longitudinal axis of the cylindrical tube and a distal end and proximal end, the distal end of the axle being axially spaced apart from the magnetic stir bar; and
   a first radial spacer disposed adjacent the distal end of the axle and a second radial spacer disposed adjacent the proximal end of the cylindrical tube, each radial spacer having an outer radial surface and an inner radial surface that is disposed adjacent the axle, at least a portion of the outer radial surface engaging the inner diameter of the cylindrical hollow tube;
   wherein the axle is stationary and the cylindrical tube rotates a bout its longitudinal axis and the longitudinal axis of the axle in response to a rotational magnetic force received by the magnetic stir bar
   further comprising a cap comprising an end wall and a cylindrical side wall that extends axially from an edge of the end wall, the cap further defining an opening in a center of the end wall, wherein the side wall engages the proximal end of the cylindrical tube and the proximal end of the axle extends through the opening in the center of the end wall of the cap, and the cap rotates with the cylindrical tube about the axle.

2. The impeller of claim 1, wherein the side wall defines a plurality of screw threads and the proximal end of the cylindrical tube defines a plurality of mating screw threads for engaging the screw threads of the side wall of the cap.

3. The impeller of claim 1, further comprising a dampening ring disposed around a portion of the axle, wherein the dampening ring has a diameter that is greater than a diameter of the opening in the end wall of the cap and is disposed axially adjacent an axial inner surface of the end wall, the axial inner surface of the end wall facing towards the distal end of the hollow cylindrical tube.

4. The impeller of claim 3, wherein the dampening ring comprises an elastomeric material.

5. The impeller of claim 3, wherein an axial position of the dampening ring along the axle is adjustable.

6. The impeller of claim 1, wherein one or more additional radial spacers are disposed axially between the first and the second radial spacers, each of the one or more additional radial spacers having an outer radial surface, wherein at least a portion of the outer radial surface engages the inner diameter of the cylindrical tube.

7. The impeller of claim 6, wherein the one or more additional radial spacers are axially spaced apart from each other and the first and second radial spacers so as to evenly distribute the mass of the radial spacers along the axle.

8. The impeller of claim 7, wherein the spacing between the one or more additional radial spacers is selected to maintain smooth and stable rotation about the axle.

9. The impeller of claim 1, wherein the radial spacers comprise ball bearings.

10. The impeller of claim 1, wherein the radial spacers comprise nuts.

11. The impeller of claim 1, further comprising first and second axial stop members, the first axial stop member being disposed axially adjacent and distally of the first radial spacer and the second axial stop member being disposed axially adjacent and distally of the second radial spacer, wherein the axial stop members prevent axial movement of the radial spacers toward the distal end of the axle.

12. The impeller of claim 1, wherein the magnetic stir bar is disposed 1 millimeter below the distal end of the axle.

13. The impeller of claim 1, wherein a distal surface of the second radial spacer is disposed 1 mm to 5 mm from the distal end of the tube.

14. A bioreactor system comprising:
a bioreactor vessel having a bottom surface and one or more side walk extending from the bottom surface, the one or more side walls defining at least one central opening axially opposite the bottom surface;
a vessel cap configured for engaging the one or more side walls to close off the central opening of the vessel, the vessel cap comprising a top surface and one or more side walls that extend from the top surface and engage with the one or more side walls of the vessel;
an impeller comprising:
a cylindrical hollow tube having a proximal end and a distal end along a longitudinal axis extending through the cylindrical tube, the cylindrical tube defining an inner diameter;
a magnetic stir bar disposed adjacent the distal end of the tube; an axle extending through a portion of the length of the cylindrical tube, the axle having a longitudinal axis that is collinear with the longitudinal axis of the cylindrical tube and a distal end and proximal end, the distal end of the axle being axially spaced apart from the magnetic stir bar; and
a first radial spacer disposed adjacent the distal end of the axle and a second radial spacer disposed adjacent the proximal end of the cylindrical tube, each radial spacer having an outer radial surface that engages the inner diameter of the cylindrical tube and an inner radial surface that is disposed adjacent the axle, at least a portion of the outer radial surface engaging the inner diameter of the cylindrical hollow tube;
wherein the axle is stationary and the cylindrical tube rotates about its longitudinal axis and the longitudinal axis of the axle in response to a rotational magnetic force received by the magnetic stir bar, and
wherein the proximal end of the axle extends through an opening defined in the top surface of the vessel cap and is secured relative to the top surface of the vessel cap, and the distal end of the cylindrical hollow tube is spaced apart from and axially above the bottom surface of the bioreactor vessel
further comprising a cap comprising an end wall and a cylindrical side wall that extends axially from an edge of the end wall, the cap further defining an opening in a center of the end wall, wherein the side wall engages the proximal end of the cylindrical tube and the proximal end of the axle extends through the opening in the center of the end wall of the cap, and the cap rotates with the cylindrical tube about the axle.

15. The bioreactor system of claim 14, further comprising a temperature control system, the temperature control system comprising:
an open ended container in which a liquid is disposed;
a pump;
a temperature control source; and
one or more conduits extending between the open ended container, the pump, and the temperature control source, wherein the bottom surface and at least a portion of the side walls of the vessel are disposable within the open ended container such that the liquid surrounds the portion of the side walls of the vessel, and the pump causes the liquid to flow between the open ended container and the temperature control source.

16. The bioreactor system of claim 15, wherein the temperature control source comprises a second container and a heater plate, wherein the second container is disposed on the heater plate and heat is transferred between the fluid in the second container and the heater plate.

17. The bioreactor system of claim 16, wherein the heater plate is selectably used as a heat sink or a heat source.

18. The temperature control system of claim 15, wherein the temperature control source comprises a second container and a heating plate, and the heating plate transfers heat to the liquid in the second container.

19. The bioreactor system of claim 14 further comprising an aeration system, the aeration system comprising:
an air pump;
a safety container; and
conduits extending between the air pump and the safety container and from the safety container to the vessel,
wherein the safety container defines a first port in fluid communication with the conduit extending between the pump and the safety container, a second port in fluid communication with the conduit extending between the safety container and the vessel, and a third port in fluid communication with a safety valve that opens in response to the air pressure inside of the safety container reaching a predetermined threshold and allows air to pass to the atmosphere.

* * * * *

UNITED STATES PATENT AND TRADEMARK OFFICE
CERTIFICATE OF CORRECTION

| | |
|---|---|
| PATENT NO. | : 10,900,007 B2 |
| APPLICATION NO. | : 15/780487 |
| DATED | : January 26, 2021 |
| INVENTOR(S) | : Bryan Stubblefield and Eric Gilbert |

It is certified that error appears in the above-identified patent and that said Letters Patent is hereby corrected as shown below:

In the Claims

Column 13, Line 34, delete "...more side walk extending..." and insert -- "...more side walls extending..." --, therefor.

Column 13, Line 48, delete "... tube; an axle extending..." and insert
-- "... tube;
an axle extending..." --, therefor.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*